United States Patent [19]

Girten et al.

[11] Patent Number: 5,597,843
[45] Date of Patent: Jan. 28, 1997

[54] USE OF A SUBSTITUTED 1,3-BENZODIOXOLE TO REDUCE A WASTING CONDITION

[75] Inventors: Beverly E. Girten, San Diego; Ronald R. Tuttle, Escondido, both of Calif.

[73] Assignee: Houghten Pharmaceuticals, San Diego, Calif.

[21] Appl. No.: 485,609

[22] Filed: Jun. 7, 1995

[51] Int. Cl.$^6$ .......................... A61K 31/42; A61K 31/36
[52] U.S. Cl. .............................. 514/376; 514/465
[58] Field of Search ..................... 514/376, 465

[56] References Cited

U.S. PATENT DOCUMENTS

| | | | |
|---|---|---|---|
| 5,061,727 | 10/1991 | Bloom et al. | 514/465 |
| 5,087,472 | 2/1992 | Nissen | 514/557 |
| 5,106,867 | 4/1992 | Bloom et al. | 514/465 |
| 5,151,439 | 9/1992 | Bloom et al. | 514/376 |
| 5,348,979 | 9/1994 | Nissen et al. | 514/557 |

OTHER PUBLICATIONS

Bloom, Jonathan D. et al., "Disodium (R,R)-5-[[2-(3-Chlorophenyl)-2-hydroxyethyl]-amino]propyl-1,3-benzodioxole-2,2-dicarboxylate (CL316,243). A Potent β-Adrenergic Agonist Virtually Specific for β$_3$ Receptors." *J. Med. Chem.* 35:3081-3084 (1992).

Kim, Yong S. and Sainz, Roberto D. "β-Adrenergic Agonists and Hypertrophy of Skeletal Muscles." *Life Sci.* 50:397-407 (1992).

Frishman, William H. "Pindolol: A New β-Adrenoceptor Antagonish with Partial Agonist Activity." *New England J. Med.* 308:940-944 (1983).

Arch, J. R. S. "The Brown Adipocyte β-Adrenoceptor." *Proceedings Nutri. Soc.* 48:215-223 (1989).

Arch, J. R. S. et al., "Atypcial β-adrenoceptor on Brown Adipocytes as Target for Anti-Obesity Drugs." *Nature* 309:163-165 (1984).

Tan, Suon and Curtis-Prior, P. B. "Characterization of the Beta-Adrenoceptor of the Adipose Cell of the Rat." *Inter. J. Obesity* 7:409-414 (1983).

Bond, Richard A. and Clarke, David E. "Agonist and Antagonist Characterization of a Putative Adrenoceptor with Distinct Pharmacological Properties from the α-and β-subtypes." *Br. J. Pharmacol.* 95:723-734 (1988).

Bond, Richard A. and Clarke, David E. "A Response to Isoprenaline Unrelated to α-and β-Adrenoceptor Agonism." *Br. J. Pharmac.* 91:683-686 (1987).

Arch, Jonathan R. S. "Thermogenic and Antiobesity Activity of a Novel β-Adrenoceptor Agonist (BRL 26830A) in Mice and Rats." *Amer. J. Clin. Nutri.* 38:549-558 (1983).

Féve, Bruno et al., "Differential Regulation of β$_1$-and β$_2$-Adrenergic Receptor Protein and mRNA Levels by Glucocorticoids during 3T3-f442A Adipose." *J. Biol. Chem.* 265:16343-16349 (1990).

Marullo, Stefano et al., "Selective Binding of Ligands to β1, β2 or Chimeric β1/β2-Adrenergic Receptors Involves Multiple Subsites." *EMBO. J.* 9:1471-1476 (1990).

Tate, Keri M. et al., "Expression of Three Human β-adrenergic-receptor Subtypes in Transfected Chinese Hamster Ovary Cells." *Eur. J. Biochem.* 196:357-361 (1991).

Emorine, Laurent J. et al., "Molecular Characterization of the Human β$_3$-Adrenergic Receptor." *Science* 245:1118-1121 (1989).

Emorine, Laurent J. et al., "Structural Basis for Functional Diversity of β$_1$-, β$_2$-and β$_3$-Adrenergic Receptors." *Biochem. Pharmacol.* 41:853-859 (1991).

Challiss, R. A. John et al., "An Investigation of the β-Adrenoceptor that Mediates Metabolic Responses to the Novel Agonist BRL28410 in Rat Soleus Muscle." *Biochem. Pharmacol.* 37:947-950 (1988).

*Primary Examiner*—Raymond Henley, III
*Attorney, Agent, or Firm*—Campbell & Flores LLP

[57] ABSTRACT

The present invention provides a method of reducing a wasting condition, which can occur due to a pathology or to a particular physiologic or metabolic state in a subject, by administering to the subject a substituted 1,3-benzodioxole.

10 Claims, 2 Drawing Sheets

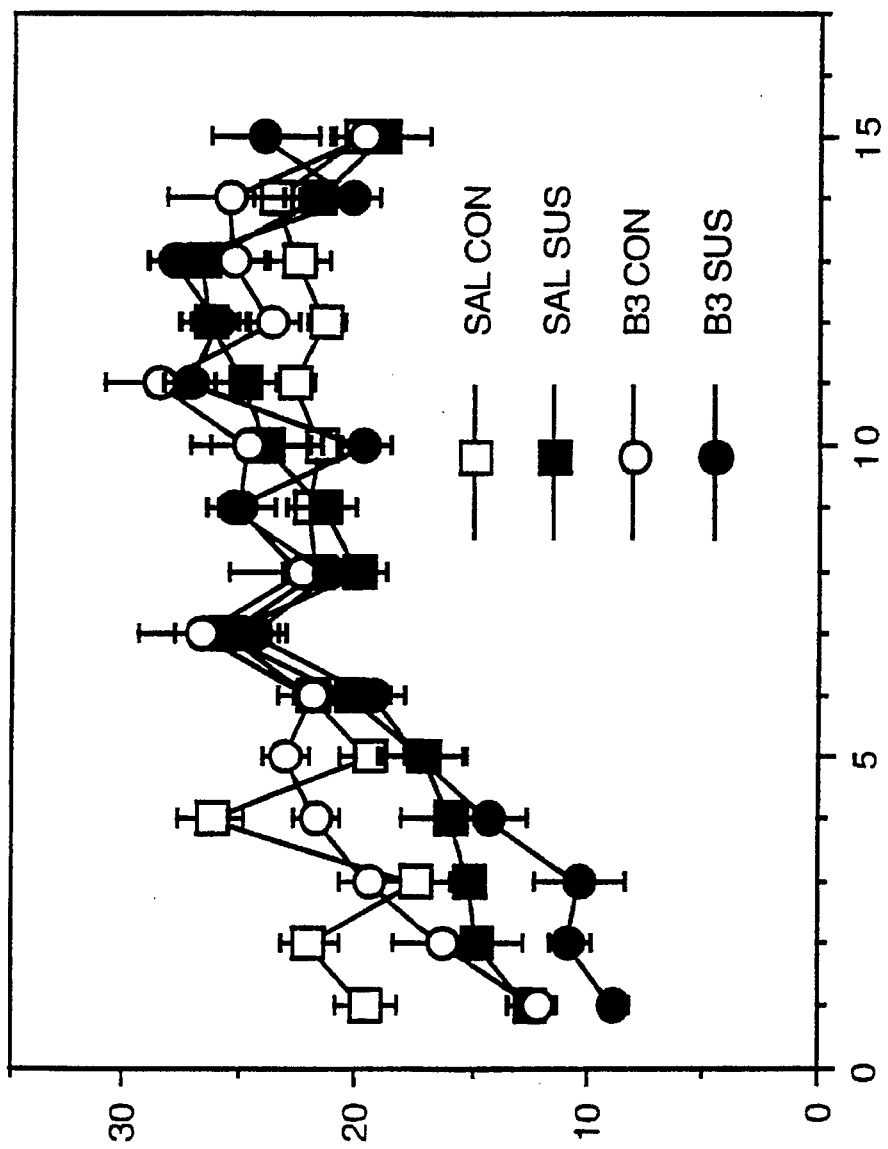

USE OF A SUBSTITUTED 1,3-BENZODIOXOLE TO REDUCE A WASTING CONDITION

BACKGROUND OF THE INVENTION

1. Field of the Invention

The present invention relates generally to the field of medicine and more specifically to the use of a substituted 1,3-benzodioxole to reduce a wasting condition in a subject.

2. Background Information

Various pathologic, physiologic and metabolic states in a subject can produce a wasting condition that is characterized, in part, by a progressive loss of body, organ or tissue mass. A wasting condition can occur as a result of a pathology such as cancer or can be due to a physiologic or metabolic state such as the disuse deconditioning that can occur, for example, due to prolonged bed rest or to the weightlessness associated with space flight.

In most cases, minimal loss of body mass is of little concern. For example, a minimal loss of body mass can occur in a subject having a brief illness but an otherwise normal nutritional status. In this case, the lost body mass is quickly regained after the illness runs its course. Loss of body mass can become critical, however, during a prolonged illness, where nutritional depletion can occur, or when a weight bearing load is removed from the musculo-skeletal system for an extended period of time. Removal of a weight bearing load can occur, for example, due to long term bed rest, immobilization of a limb or simulated or actual weightlessness such as during space flight.

The loss of body mass that occurs during a wasting condition can be characterized by a loss of total body weight, a loss of organ weight such as a loss of bone or muscle mass or to a decrease in tissue protein. In addition, the loss of body mass associated with a wasting condition can be localized or systemic. For example, localized loss of body mass can occur due to denervation of a muscle or to the disuse deconditioning that occurs when a limb is immobilized in a cast. Systemic loss of body mass can result, for example, due to the disuse deconditioning that occurs during space flight or due to a pathology such as cancer.

A wasting condition, if unabated, can have dire health consequences. For example, the changes that occur during a wasting condition can lead to a weakened physical state that is detrimental to an individual's health. The severe wasting or cachexia associated with cancer, for example, can prolong patient convalescence and decrease the patient's quality of life.

Three general approaches have been utilized to reduce a wasting condition in a subject. One approach has been to alter the systemic stress response that is induced due to acute injury or illness. For example, an attempt has been made to manipulate the signals mediated by cytokines or lipids, which are involved in regulating the stress response.

Another approach to reduce a wasting condition has been to administer supplemental nutrition. In many cases, however, even when a subject is maintained on a program of total parenteral nutrition over several weeks, loss of body mass continues and no increase in muscle mass occurs. Thus, simple replacement of any deficient caloric intake is insufficient, alone, to alleviate an undesirable loss of body mass.

Nutritional supplementation has been used in combination with the administration of anabolic agents in an attempt to reduce wasting. This combined approach currently is the preferred method of treatment and can effectively counteract the loss of body mass that occurs due to acute illness, disuse deconditioning and cachexia.

Various anabolic agents, including anabolic steroids, growth hormone, insulin-like growth factors and beta adrenergic agonists, have been used in the combined modality protocol. Unfortunately, the usefulness of anabolic agents is limited by undesirable side effects. For example, anabolic steroids can cause adverse effects in the liver and in the cardiovascular and reproductive systems of a treated individual and can affect the psychological status of the subject. Other anabolic agents such as growth hormone and insulin-like growth factors can induce diabetes, hypothyroidism and arthritis as well as acromegaly, which is associated with myopathy, peripheral neuropathy and cardiac disease.

The $\beta 2$ adrenergic agonists clenbuterol and salbutamol are anabolic agents that can reduce weight loss, particularly loss of muscle mass and bone density (see Kim and Sainz, Life Sci. 50:397–407 (1992)). However, $\beta 2$ agonists can produce undesirable side effects, including increased heart rate, decreased blood pressure or muscle tremor, in a treated subject. These agents also can produce undesirable behavioral changes. Thus, a need exists to identify pharmaceutical agents that effectively reduce a wasting condition in a subject without producing significant adverse side effects. The present invention satisfies this need and provides related advantages as well.

SUMMARY OF THE INVENTION

The present invention provides a method for reducing a wasting condition in a subject by administering a substituted 1,3-benzodioxole, which is a $\beta 3$ adrenergic agonist, to the subject. The invention provides, for example, the use of a substituted 5-(2-((2-aryl-2-hydroxyethyl)amino)propyl)-1,3-benzodioxole to reduce the loss of body mass associated with a wasting condition caused by a pathologic, physiologic or metabolic state in a subject. The invention provides methods for reducing a wasting condition due, for example, to cancer, disuse deconditioning, denervation of a muscle or an acute inflammatory response in a subject.

BRIEF DESCRIPTION OF THE DRAWINGS

FIG. 2 shows the effect of administering HP186 on the mean food consumption (± SE; grams; N=8) of rats over 14 day period of suspension of the hind limbs. Groups were treated as described in FIG. 1.

DETAILED DESCRIPTION OF THE INVENTION

Figure 1:
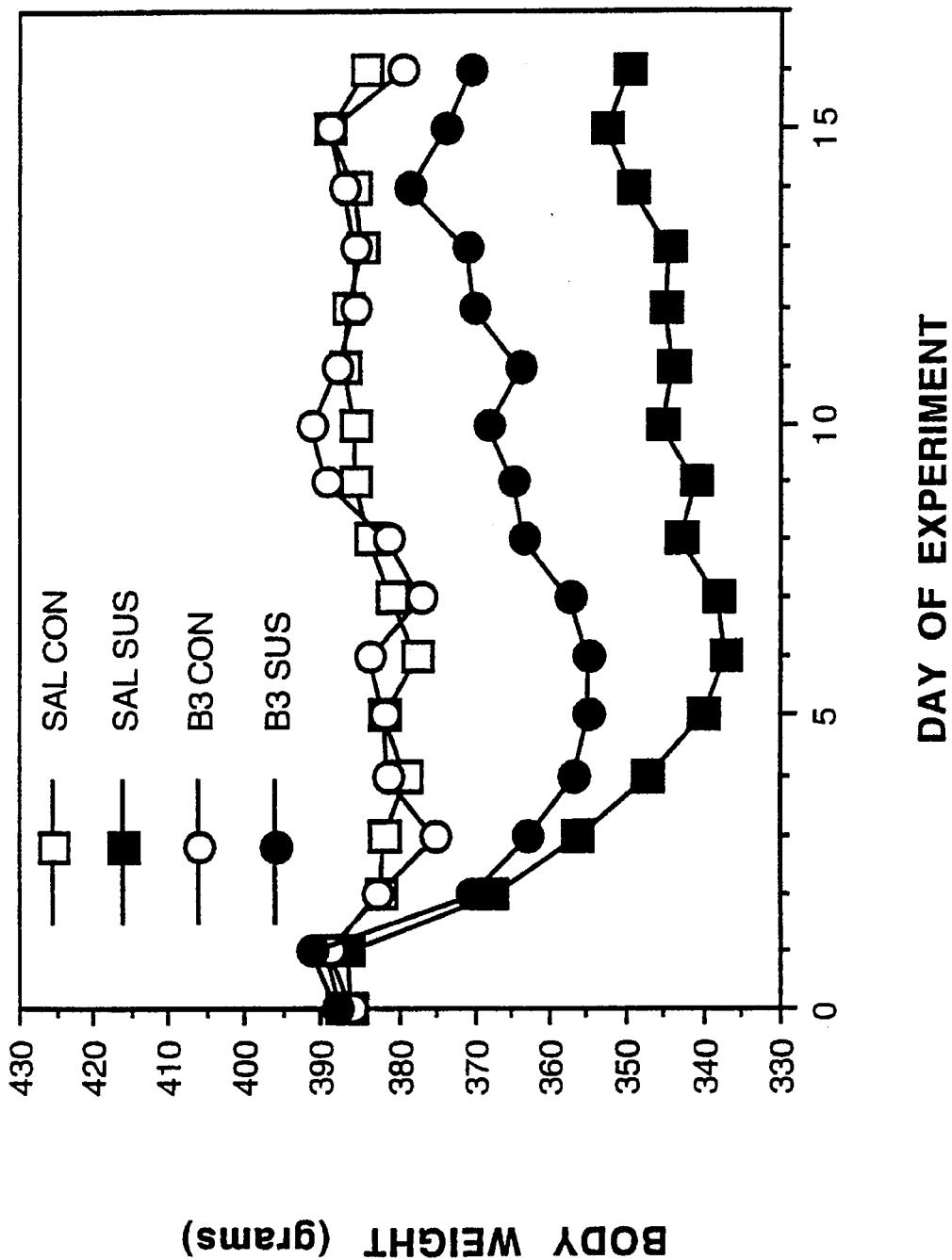
FIG. 1 demonstrates the effectiveness of HP186, which is a $\beta 3$ adrenergic receptor-selective agonist, in reducing the loss of body weight that occurs in rats due to disuse deconditioning. Body weights were measured beginning two days prior to initiating suspension of the hind limbs (day 0). Beginning on day 2, HP186 (2 mg/kg) or saline was administered ip, 2×/day, approximately 7 hr apart, over a period of 14 days (days 2–15), except that only one injection was made on day 11. Data are expressed as mean body weight ± standard error of the mean (SE; grams; N=8) versus the number of days. "SAL" indicates rats were injected with saline; "B3" indicates rats were injected with HP186; "CON" indicates rats were not suspended; "SUS" indicates rats were suspended.

The present invention provides methods for reducing a wasting condition in a subject by administering to the subject a substituted 1,3-benzodioxole. The substituted 1,3-benzodioxoles used herein have been described previously (see Bloom et al., J. Med. Chem. 35:3081–3084 (1992); U.S. Pat. No. 5,061,727, issued Oct. 29, 1991; U.S. Pat. No. 5,106,867, issued Apr. 21, 1992; and U.S. Pat. No. 5,151, 439, issued Sep. 29, 1992, each of which is incorporated herein by reference).

A substituted 1,3-benzodioxole useful in the present invention has the general structure:

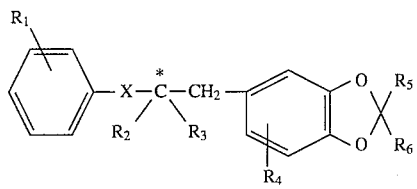

where X is

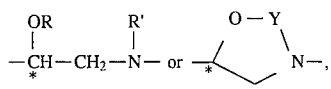

$R_1$ and $R_4$ are one or more groups that are the same or different and are selected from the group consisting of hydrogen, $C_1$ to $C_4$ alkyl and $C_1$ to $C_4$ acyl and Y is selected from the group consisting of carbonyl and thiocarbonyl;

$R_2$ and $R_3$ are the same or different and are selected from the group consisting of hydrogen and $C_1$ to $C_4$ alkyl; $R_5$ and $R_6$ are selected from the group consisting of hydrogen, carboxy, alkoxycarbonyl, hydroxymethyl, $CH_2OCH_2COOR_7$ and $CH_2OCH_2CH_2OR_7$, where $R_7$ is hydrogen or $C_1$ to $C_4$ alkyl;

with the provision that $R_5$ and $R_6$ may not both be hydrogen;

and the pharmaceutically acceptable salts and esters thereof, the enantiomers thereof, the racemic mixtures thereof and the diastereomeric mixtures thereof (U.S. Pat. No. 5,061,727, supra, 1991).

A substituted 5-(2-((2-aryl-2-hydroxyethyl) amino)pro-pyl)-1,3-benzodioxole can be particularly useful for reducing a wasting condition in a subject. For example, (R,R)-5-(2-((2-(3-chlorophenyl)-2-hydroxyethyl) amino)propyl)-1, 3-benzodioxole-2-2-dicarboxylate (HP186 ), having the structure:

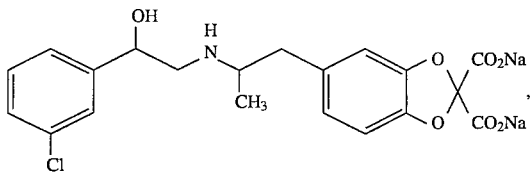

can be used to reduce the loss of body mass associated with a wasting condition (see Example I).

As disclosed herein, a substituted 1,3-benzodioxole, when administered to a subject experiencing a wasting condition, can reduce the rate or amount of body weight loss as compared to the rate or amount of body weight loss that occurs in a subject not receiving the agent (see Example I). For convenience, reference is made generally to "reducing a wasting condition." As used herein, the term "reducing" has its commonly understood meaning of lessening or decreasing. The term "a wasting condition" is used broadly to mean an abnormal, measurable decrease in body, organ or tissue weight. Such an abnormal decrease, which can be due, for example, to a decrease in muscle or bone mass or tissue protein, can be measured by weighing the subject or by measuring the circumference, for example, of one or more limbs of the subject.

The abnormal, measurable decrease in body, organ or tissue weight associated with a wasting condition can occur due to various pathologic, physiologic and metabolic states, which are generally characterized in being variant from the physiologic and metabolic state of a normal, healthy individual. Thus, the term "wasting condition" refers, for example, to the unwanted decrease in muscle mass that occurs due to prolonged bed rest or immobilization of a limb in a cast or due to denervation of a muscle, to the unhealthy decrease in body weight that can occur during an acute inflammatory response or that occurs in a cancer patient as a result of cachexia or of radiotherapy or chemotherapy, or to the undesirable decrease in body mass due to simulated or actual weightlessness such as occurs during space travel.

As demonstrated in Example I, a substituted 1,3-benzodioxole effectively reduced the undesirable loss of body weight that occurs due to hindlimb suspension of rats, which is a model for disuse deconditioning. For example, administration of HP186 ("B3") to suspended rats reduced the rate and the total amount of body weight loss by the rats as compared to control rats, which received saline ("SAL"; FIG. 1, compare "B3 SUS" and "SAL SUS"). Remarkably, the reduction in the loss of body weight observed in the HP186-treated rats was not due to increased food consumption, which was not significantly different among the various experimental groups (see FIG. 2).

The discovery that administration of a substituted 1,3-benzodioxole can reduce a wasting condition was unexpected because related compounds previously found use in treating obesity (see U.S. Pat. No. 5,061,727). Prior to the present disclosure, substituted 1,3-benzodioxoles were known to be useful for causing weight loss. In contrast, the present invention provides methods of using a substituted 1,3-benzodioxole to reduce a loss of body mass that occurs in a wasting condition.

Substituted 1,3-benzodioxoles are β3 agonists that bind the β3 adrenergic receptor and stimulate adipocyte lipolysis in rats (Bloom et al., supra, 1992; see, also, U.S. Pat. No. 5,061,727, supra, 1991). Three families of β adrenergic receptors, designated β1, β2 and β3, are known. In general, β1 agonists increase heart rate upon binding β1 adrenergic receptors and β2 agonists stimulate glycogen breakdown upon binding β2 receptors. β2 agonists are anabolic agents that have been used to reduce weight loss, including loss of muscle mass. However, the use of most β2 agonists is limited because many of them also can bind the β1 adrenergic receptor and, therefore, can cause increased heart rate as a side effect in a subject.

Substituted 1,3-benzodioxoles are β3 agonists that bind with a much higher affinity to the β3 receptor than to the β1 and β2 adrenergic receptors. As a result of their relative selectivity for binding β3 adrenergic receptors, the use of a substituted 1,3-benzodioxole in a subject does not significantly increase heart rate or muscle tremor, which is an undesirable side effect caused by binding of a β agonist to the β1 or β2 adrenergic receptors (Bloom et al., supra, 1992). Thus, substituted 1,3-benzodioxoles can be used to treat obesity without causing concern for the undesirable side effects associated with the use of β1 or β2 agonists.

As disclosed herein, administration of a substituted 1,3-benzodioxole to a subject having a wasting condition can reduce the loss of body mass that otherwise would occur in the subject. Use of a substituted 1,3-benzodioxole to reduce a wasting condition is advantageous over previous methods using, for example, β2 agonists because the selectivity of a substituted 1,3-benzodioxole for β3 adrenergic receptors minimizes the likelihood that non-specific binding to a β1 or β2 receptor will occur and produce undesirable side effects in a treated subject.

The use of a pharmaceutical composition comprising a substituted 1,3-benzodioxole and a pharmaceutically acceptable carrier for the purpose of reducing a wasting condition in a subject is disclosed herein. Pharmaceutically acceptable carriers are well known in the art and include aqueous solutions such as physiologically buffered saline or other solvents or vehicles such as glycols, glycerol, oils such as corn oil or olive oil or injectable organic esters.

A pharmaceutically acceptable carrier can contain physiologically acceptable compounds that act, for example, to stabilize a substituted 1,3-benzodioxole or increase the absorption of the agent. Such physiologically acceptable compounds include, for example, carbohydrates such as glucose, sucrose or dextrans, antioxidants such as ascorbic acid or glutathione, chelating agents, low molecular weight proteins, or other stabilizers or excipients. One skilled in the art would know that the choice of a pharmaceutically acceptable carrier, including a physiologically acceptable compound, depends, for example, on the route of administration of the substituted 1,3-benzodioxole and on the particular physico-chemical characteristics of the specific substituted 1,3-benzodioxole.

The invention provides methods of administering a pharmaceutical composition comprising a substituted 1,3-benzodioxole to a subject in order to reduce a wasting condition in the subject. The composition can be administered to a subject to reduce the wasting that can occur due, for example, to an acute inflammatory response, to cachexia, or to prolonged disuse of a muscle or muscle group. A pharmaceutical composition comprising a substituted 1,3-benzodioxole can be administered to a subject by various routes including, for example, orally or parenterally, such as intravenously, intramuscularly or subcutaneously. Furthermore, the composition can be administered by injection or intubation.

A wasting condition can lead to severe disability or death of a subject. The wasting can be localized as occurs, for example, when a limb is immobilized in a cast, or can be systemic as occurs, for example, due to the cachexia associated with cancer or during prolonged bed rest or weightlessness. Although wasting can be localized or systemic, a substituted 1,3-benzodioxole generally will be administered such that the agent is distributed systemically in the subject.

It is further contemplated that a useful substituted 1,3-benzodioxole can be incorporated into a food and ingested by a subject. A composition comprising a food and a substituted 1,3-benzodioxole is considered to be generally encompassed within the meaning of the term "pharmaceutical composition" as used herein. Methods for preparing such a composition are well known to those in the art and described, for example, in U.S. Pat. Nos. 5,061,727 and 5,106,867, supra.

In order to reduce a wasting condition in a subject, a substituted 1,3-benzodioxole must be administered in a therapeutically effective amount, which is about 0.01 to 100 mg/kg body weight per dose. Thus, the compositions are useful as medicaments that can be administered to a subject for the purpose of reducing a wasting condition in the subject.

A therapeutically effective amount of a substituted a substituted 1,3-benzodioxole can be administered to a subject as a single dose, for example, as a bolus or by infusion over a relatively short period of time or in a food. A therapeutically effective amount also can be administered as a series of treatments in which multiple doses are administered over a more prolonged period of time (see Example I). One skilled in the art would know that the concentration of a substituted 1,3-benzodioxole required to obtain a therapeutically effective amount in a subject depends on many factors including the age, body weight and general health of the subject as well as the route of administration and the number of treatments to be administered. In view of these factors, the skilled artisan would adjust the particular dose so as to obtain a therapeutically effective amount, which can reduce a wasting condition in a subject.

The following examples are intended to illustrate but not limit the invention.

EXAMPLE I

HP186 Effectively Reduces Loss of Body Weight Due to Disuse Deconditioning

This example demonstrates the effectiveness of HP186, which is a substituted 5-(2-((2-aryl-2-hydroxyethyl) amino)propyl)-1,3-benzodioxole, in reducing the loss of body weight associated with disuse deconditioning.

HP186 was prepared as described in U.S. Pat. No. 5,061,727, supra, and by Bloom et al. (supra, 1992). The disodium salt was isolated as an amorphous powder by reverse-phase column chromatography.

Disuse deconditioning was effected using the rat hindlimb suspension model, which was developed by the National Aeronautics and Space Administration as a ground based animal model for weightlessness (Morey, *Bioscience* 29:168–172 (1979), which is incorporated herein by reference). This model system involves the use of an x-y axis support system that allows a suspended rat to move freely about its cage. The tail suspension methodology utilizes adhesive foam padded traction tape (Fas-trac) and bias cut stockette. This combination, which results in unloading of the hindlimbs, allows the rat's weight support to be distributed and does not inhibit blood circulation in the tail.

Hindlimb unloading leads to rapid loss of muscle mass in hindlimb muscles such as the soleus and to demineralization of hindlimb bones. When young, growing animals are used, the rate of growth is slowed, whereas when adult animals are used, there is a loss of body weight during the first few days of the experiment. All experiments described herein used adult rats.

Thirty-two adult male Sprague-Dawley rats (mean weight=387 grams) were randomly assigned to four groups as follows: 1) a saline control group (SAL CON), which were injected with saline but were not suspended; 2) a saline suspended group (SAL SUS), which were injected with saline and were suspended; 3) a β3 control group (B3 CON), which were injected with the substituted 5-(2-((2-aryl-2-hydroxyethyl)amino)propyl)-1,3-benzodioxoleβB3adrenergic agonist, HP186, but were not suspended; and 4) a β3 suspended group (B3 SUS), which were injected with HP186 and were suspended (see FIGS. 1 and 2).

Body weight and food consumption measurements were begun two days prior to suspension (day 0) and were made every day thereafter throughout the treatment period. As compared to control rats, which received saline, administration of HP186 reduced the loss of body weight due to hindlimb suspension (see FIG. 1; compare SAL SUS and B3 SUS). A reduction in the rate of loss of body weight was evident by the second day of treatment with HP186 (see FIG. 1; day 3) and the reduction in weight loss of the HP186-treated animals as compared to the control animals was maintained throughout the treatment period (SAL SUS and B3 SUS; FIG. 1). Administration of HP186 did not affect the amount of food consumption by the rats (see FIG. 2).

At the end of the treatment period, the rats were sacrificed and various tissues and organs were removed and weighed. Administration of HP186 significantly reduced the weight of the fat pads in both the unsuspended and suspended groups as compared to the saline controls (see Table 1). This result correlates with the known effect of substituted 1,3-benzodioxoles to stimulate rat adipocyte

TABLE 1

| Tissue | Organ and Tissue Wet Weights (grams) | | | |
|---|---|---|---|---|
| | SAL CON | SAL SUS | β-3 CON | β-3 SUS |
| Fat Pads | 3.129 (0.180) | 2.068 (0.085)* | 2.374 (0.137)* | 1.596 (0.131)*# |
| Heart | 1.360 (0.023) | 1.237 (0.035)* | 1.347 (0.027) | 1.318 (0.036) |
| Spleen | 0.683 (0.020) | 0.637 (0.022) | 0.713 (0.033) | 0.683 (0.025) |
| Plantaris | 0.820 (0.040) | 0.670 (0.042) | 0.792 (0.037) | 0.740 (0.036) |
| Soleus | 0.173 (0.004) | 0.120 (0.004)*# | 0.177 (0.006) | 0.137 (0.011)*# |

Numbers in parentheses represent standard error of the mean.
*indicates significantly less than SAL CON counterpart ($p \leq 0.05$).
indicates significantly less than β-3 CON counterpart ($p \leq 0.05$).

lipolysis (see Bloom et al., supra, 1992). Administration of HP186 also attenuated the loss of organ weight and muscle mass, with particular benefit observed in the soleus muscle and the heart (Table 1).

These results demonstrate that a substituted 1,3-benzodioxole can effectively reduce the unwanted loss of body mass that otherwise occurs as a result of disuse deconditioning. Furthermore, the majority of the loss of body mass is due to loss of fat or adipose tissue rather than to loss of protein, which provides the majority of the mass and structure of muscle tissue and organs.

Although the invention has been described with reference to the examples provided above, it should be understood that various modifications can be made without departing from the spirit of the invention. Accordingly, the invention is limited only by the following claims.

We claim:

1. A method of reducing a wasting condition in a subject, comprising administering to a subject having a wasting condition a therapeutically effective amount of a substituted 1,3-benzodioxole.

2. The method of claim 1, wherein said substituted 1,3-benzodioxole is a substituted 5-(2-((2-aryl-2-hydroxyethyl)amino)propyl)-1,3-benzodioxole.

3. The method of claim 2, wherein said 5-(2-((2-aryl-2-hydroxyethyl)amino)propyl-1,3-benzodioxole is (R,R)-5-(2-((2-(3-chlorophenyl)-2-hydroxyethyl)amino)propyl)-1,3-benzodioxole-2-2-dicarboxylate, having the structure:

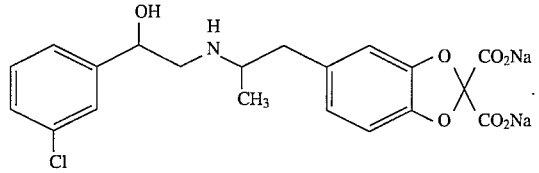

4. The method of claim 1, wherein said wasting condition is due to a pathology.

5. The method of claim 4, wherein said pathology is cancer.

6. The method of claim 4, wherein said pathology is an acute inflammatory response.

7. The method of claim 1, wherein said wasting condition is due to disuse deconditioning.

8. The method of claim 7, wherein said disuse deconditioning occurs due to weightlessness.

9. The method of claim 7, wherein said disuse deconditioning occurs due to immobilization.

10. The method of claim 1, wherein said wasting condition is due to muscle denervation.

* * * * *

UNITED STATES PATENT AND TRADEMARK OFFICE
CERTIFICATE OF CORRECTION

PATENT NO. : 5,597,843
DATED : Jan. 28, 1997
INVENTOR(S) : Girten et al.

It is certified that error appears in the above-identified patent and that said Letters Patent is hereby corrected as shown below:

In column 3, line 18, please insert --* indicates a carbon atom having a center of asymmetry.--

In column 5, line 53, please delete "a substituted".

Signed and Sealed this

Seventh Day of March, 2000

Attest:

Q. TODD DICKINSON

Attesting Officer

Commissioner of Patents and Trademarks